(12) United States Patent
Springhorn et al.

(10) Patent No.: US 7,628,900 B2
(45) Date of Patent: Dec. 8, 2009

(54) SENSOR ELEMENT

(75) Inventors: Carsten Springhorn, Stuttgart (DE);
Johannes Kanters, Yokohama (JP);
Lothar Diehl, Gerlingen (DE)

(73) Assignee: Robert Bosch GmbH, Stuttgart (DE)

( * ) Notice: Subject to any disclaimer, the term of this patent is extended or adjusted under 35 U.S.C. 154(b) by 860 days.

(21) Appl. No.: 10/500,661

(22) PCT Filed: Oct. 22, 2002

(86) PCT No.: PCT/DE02/03975

§ 371 (c)(1),
(2), (4) Date: Feb. 25, 2005

(87) PCT Pub. No.: WO03/060502

PCT Pub. Date: Jul. 24, 2003

(65) Prior Publication Data

US 2005/0161324 A1      Jul. 28, 2005

(30) Foreign Application Priority Data

Jan. 3, 2002   (DE) ............................ 102 00 052

(51) Int. Cl.
*G01N 27/26* (2006.01)

(52) U.S. Cl. .................. 204/426; 204/421; 204/424

(58) Field of Classification Search ............. 204/424, 204/421, 426
See application file for complete search history.

(56) References Cited

U.S. PATENT DOCUMENTS

| | | | |
|---|---|---|---|
| 4,839,019 A | 6/1989 | Takahama et al. | |
| 4,883,947 A * | 11/1989 | Murase et al. | 219/553 |
| 6,338,782 B1 * | 1/2002 | Imamura et al. | 204/424 |
| 2002/0175077 A1 * | 11/2002 | Wahl et al. | 204/424 |

FOREIGN PATENT DOCUMENTS

| | | |
|---|---|---|
| DE | 198 33 453 | 6/2000 |
| DE | 198 57 468 | 6/2000 |
| DE | 199 52 595 | 11/2000 |
| JP | 8315967 | 11/1996 |
| JP | 11023516 | 1/1999 |
| JP | 2001183334 | 7/2002 |
| WO | WO 00/07005 | 2/2000 |
| WO | WO 01/29546 | 4/2001 |

* cited by examiner

*Primary Examiner*—Alex Noguerola
*Assistant Examiner*—J. Christopher Ball
(74) *Attorney, Agent, or Firm*—Kenyon & Kenyon LLP

(57) ABSTRACT

A sensor element having a layer configuration, for detecting a physical property of a gas, in particular for detecting the concentration of a gas component in an exhaust gas of an internal combustion engine. The sensor element has a measuring device, used to detect a physical property of the gas, and a heating device. The heating device includes a heater, which is electrically connected to a first heater supply lead and a second heater supply lead. The first heater supply lead is arranged in a plane of stratification between the second heater supply lead and the measuring device. The first heater supply lead is at an at least largely constant electrical potential.

10 Claims, 3 Drawing Sheets

SENSOR ELEMENT

FIELD OF THE INVENTION

The present invention relates to a sensor element.

BACKGROUND INFORMATION

A gas probe having such a sensor element is described in German Patent Application No. DE 198 57 468, for example, for use in analyzing the exhaust gas of internal combustion engines. In a conventional manner, the elongated planar sensor element is arranged in a housing that can be affixed in a measuring orifice of an exhaust pipe. On the measuring side, at an end that is exposed to the exhaust gas, the sensor element has a measuring device, which includes an electrochemical cell having a first electrode, a second electrode and a solid electrolyte situated between the first and second electrode. The first electrode is arranged in a reference-gas region introduced in the sensor element. The second electrode is mounted on an outer surface of the sensor element and is in contact with the exhaust gas via a porous protective layer.

A heating device is provided to heat the measuring device. The heating device has a meander-shaped heater (resistance heater) to which a first and a second heater supply lead are guided. The heater supply leads electrically connect the heater, which is arranged on the measuring-side end of the sensor element, to contact surfaces provided on a connection-side end lying across from the measuring-side end of the sensor element and via which the heater is electrically connected to electrical circuit elements arranged outside of the gas sensor. The heater and the two heater supply leads are arranged in a plane of stratification of the sensor element. The two heater supply leads extend in parallel to the longitudinal axis of the sensor element. Insulation layers electrically insulate the heating device from the surrounding elements.

The heater is operated in a conventional manner by the electrical circuit elements applying a voltage between the two heater supply leads. The first heater supply lead is at a constant potential, such as earth potential. Conventionally, the temperature inside the measuring device is determined with the aid of a resistance measurement, for example, and to control the heating device with the aid of the electrical circuit elements in such a way that a predefined temperature value is given inside the measuring device. The control-related potential changes at the second heater supply lead may interfere with the function of the measuring device because of induced voltage. Therefore, an electron-conducting intermediate layer, made of platinum, for example, is provided between the heating device and the measuring device, the intermediate layer being at a constant electrical potential.

It is disadvantageous in this context that the layer configuration for reducing the voltages which the heating device induces into the measuring device is expensive to produce and the additional platinum layer is costly.

SUMMARY

An example sensor element according to the present invention may have the advantage of realizing a layer configuration by which an impairment of the measuring device due to induced voltages is reduced, or avoided entirely, in a material-saving and simple manner. To this end, a first heater supply lead, which is at an at least largely constant potential, is arranged in a plane of stratification between a second heater supply lead and the measuring device. The first heater supply lead thus functions as connection lead of the heater and simultaneously shields the measuring device from induced voltages of a second heater supply lead that result from changes in the potential of the second heater supply lead occurring during operation.

If the first heater supply lead covers the full surface of at least one supply region of the sensor element, the measuring device is shielded from the second heater supply lead in an especially effective manner. To save material, the first heater supply lead may form a lattice structure.

The first heater supply lead may be advantageously arranged in such a way that the perpendicular projection of the second heater supply lead onto the plane of stratification of the first heater supply lead lies on the first heater supply lead, at least regionally.

In an especially advantageous manner, using screen printing and the indicated sequence, the following layers are applied onto a carrier foil: a second insulation layer by which the second heater supply lead and the heater are insulated from the carrier foil; the heater and the second heater supply lead; a first insulation layer by which the first heater supply lead is insulated from the second heater supply lead; the first heater supply lead; and, if appropriate, a third insulation layer, which covers the first heater supply lead. The first heater supply lead is printed directly onto a contact region of the heater and is thus electrically connected to the heater. For this reason, a recess is provided in the contact region of the heater in the first insulation layer. After printing, the carrier foil is laminated to one or a plurality of solid electrolyte foils of the measuring device, and then sintered.

As an alternative, the second insulation layer, the heater and the second heater supply lead may be applied onto the carrier foil by means of screen printing. The first heater supply lead and, if appropriate, the third insulation layer are printed onto an insulation foil using screen printing. The first heater supply lead is electrically connected to the heater by a plated through-hole in the insulation foil. After printing, the carrier foil, the insulation foil and one or a plurality of solid electrolyte foil(s) of the measuring device are laminated and then sintered.

BRIEF DESCRIPTION OF THE DRAWINGS

The present invention is explained with reference to the drawings and the following description.

DETAILED DESCRIPTION OF EXAMPLE EMBODIMENTS

Figure 1:
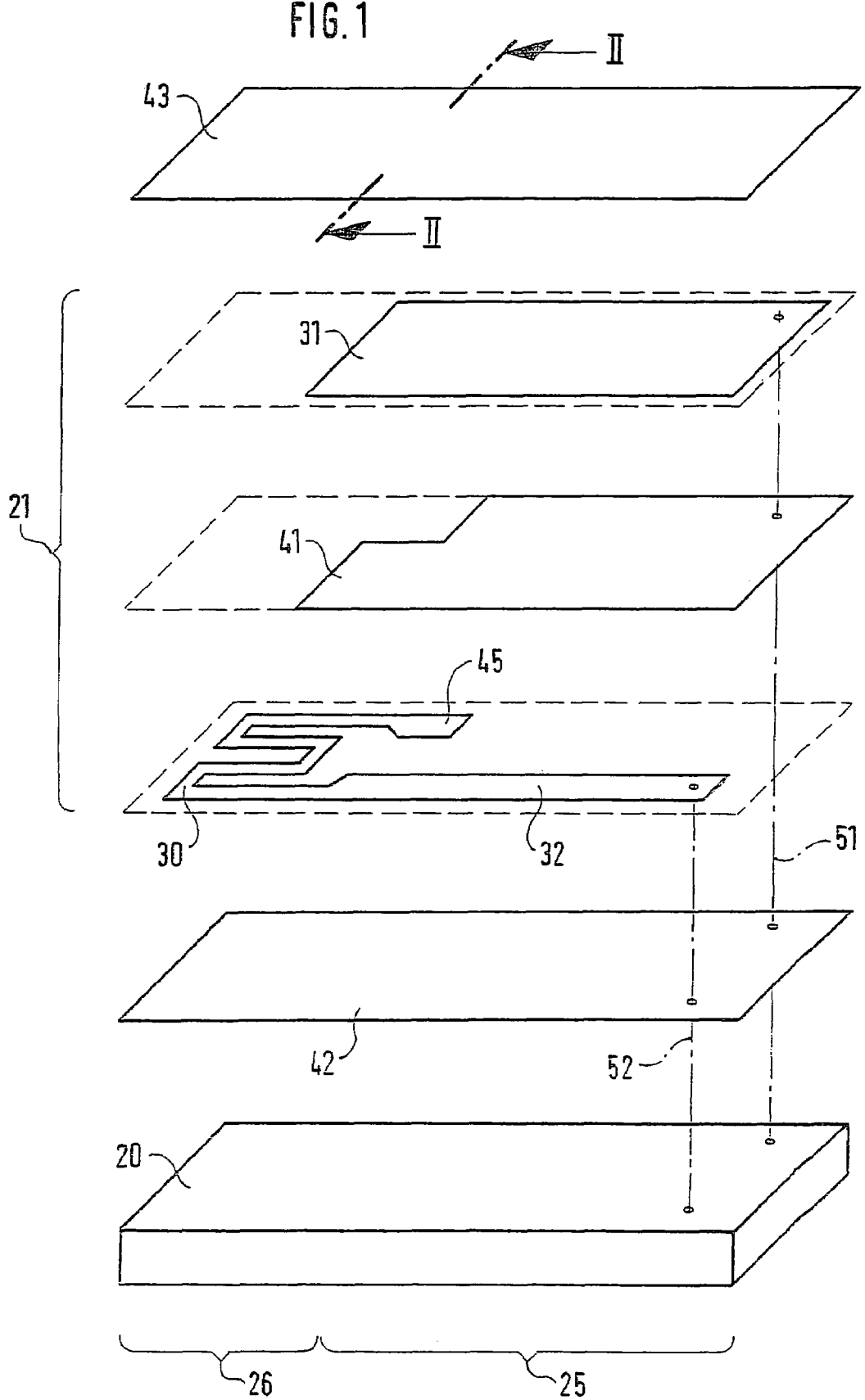
FIG. 1 shows an exploded view of a partial region of a first exemplary embodiment of a sensor element according to the present invention.
Figure 2:
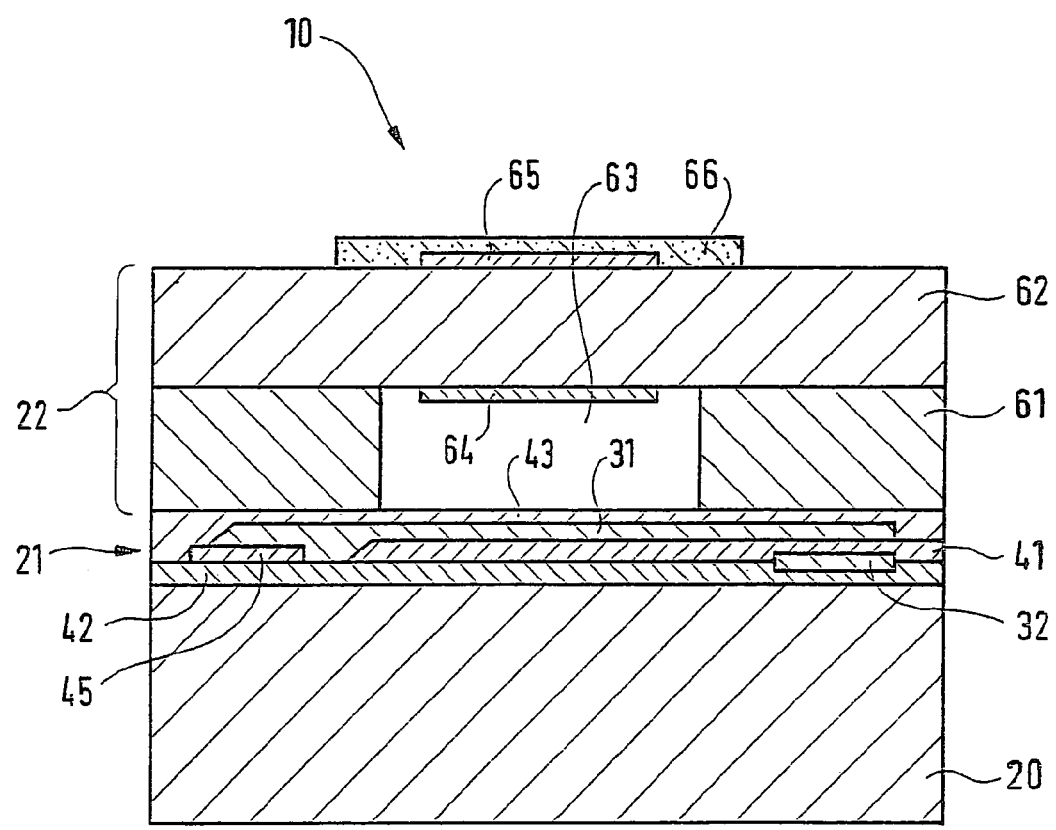
FIG. 2 shows a cross section, along line II-II in FIG. 1, through the first exemplary embodiment of the sensor element according to the present invention.

FIGS. 1 and 2 show a first exemplary embodiment of the sensor element according to the present invention. Sensor element 10 has a heating device 21, which is applied on a carrier foil 20, and a measuring device 22. Measuring device 22 of sensor element 10 is not shown in FIG. 1.

Measuring device 22, which is arranged on the measuring-side at an end 26 of sensor element 10 that is exposed to the exhaust gas, has a first solid electrolyte foil 61 and a second solid electrolyte foil 62. A reference-gas region 63 containing a reference gas has been introduced in first solid electrolyte foil 61. To this end, reference-gas region 63 is in connection with the atmospheric air via a channel in a supply region 25 of sensor element 10. In reference-gas region 63, a first electrode 64 is affixed on second solid electrolyte foil 62. A second electrode 65, covered by a porous protective layer 66 and exposed to the exhaust gas, is situated across from first electrode 64 on the outer surface of second solid electrolyte foil 62. First and second electrode 64, 65 and second solid electrolyte foil 62 form a Nernst cell. Using the voltage generated between electrodes 64, 65 in the Nernst cell, it is possible to infer the oxygen partial pressure in the exhaust gas.

However, the present invention is not restricted to a sensor element having a measuring device of the afore-described configuration. The measuring device may also include a pump cell, a combination of pump and Nernst cell (broadband lambda sensor) or some other combination of electrochemical cells. The measuring device may also have a design that realizes another measuring method, such as a resistive measurement.

Measuring device 22 is heated by heating device 21 and maintained at a constant temperature. On the basis of a temperature inside sensor element 10 detected with the aid of measuring device 22, heating device 21 is controlled by electrical circuit elements arranged outside of sensor element 10. Heating device 21 includes a heater 30, which is configured as meander-shaped resistance heater, and a first and a second heater supply lead 31, 32 arranged in supply region 25 of sensor element 10 and electrically connected to heater 30. First and second heater supply lead 31, 32, via a first and second plated through-hole 51, 52, respectively, and via a contact surface in each case (not shown) on an outer surface of carrier foil 20, connect heater 30 to the electrical circuit elements in carrier foil 20. For the heating of measuring device 22, the electrical circuit elements apply a voltage between first and second heater supply lead 31, 32. First heater supply lead 31 is constantly at ground potential; and heater 30 is energized or de-energize by a change in the potential of second heater supply lead 32.

Connecting the potential of second heater supply lead 32 may cause interference in the measuring signal of measuring device 22 due to induced voltage. To avoid induced voltages, first heater supply lead 31 is arranged in a plane of stratification between second heater supply lead 32 and measuring device 22. To this end, first heater supply lead 31 is drawn across the entire large area of sensor element 10 in supply region 25. In contrast, the width of second heater supply lead 32 is less than the corresponding width of sensor element 10. Provided between first and second heater supply lead 31, 32 is a first insulation layer 41, by which the two heater supply leads 31, 32 are electrically insulated from one another. Second heater supply lead 32 forms a continuous printed circuit trace with heater 30. First heater supply lead 31 is electrically connected to heater 30 at a contact point 45 in whose region first insulation layer 41 has a recess. A second insulation layer 42 insulates heating device 21 from carrier foil 20, and a third insulation layer 43 electrically insulates it from measuring device 22.

The sensor element is produced using screen-printing technology. Printed (in this sequence) onto carrier foil 20 for this purpose are second insulation layer 42; heater 30 having contact point 45 and second heater supply lead 32; first insulation layer 41; first heater supply lead 31; and third insulation layer 43. The electrical connection of heater 30 to first heater supply lead 31 is implemented by printing the one end of first heater supply lead 31 directly onto contact point 45 of heater 30. For this purpose, a recess is provided in this region in first insulation layer 41. Printed carrier foil 20 is laminated together with solid electrolyte foils 61, 62 of measuring device 22 and then sintered.

With the exception of the recess in the region of contact point 45 for contacting heater 30 and first heater supply lead 31, first insulation layer 41 may also extend across the entire large surface of sensor element 10, that is, it may also be provided in the region of heater 30. First heater supply lead 31 may likewise extend into the region of heater 30.

Figure 3:
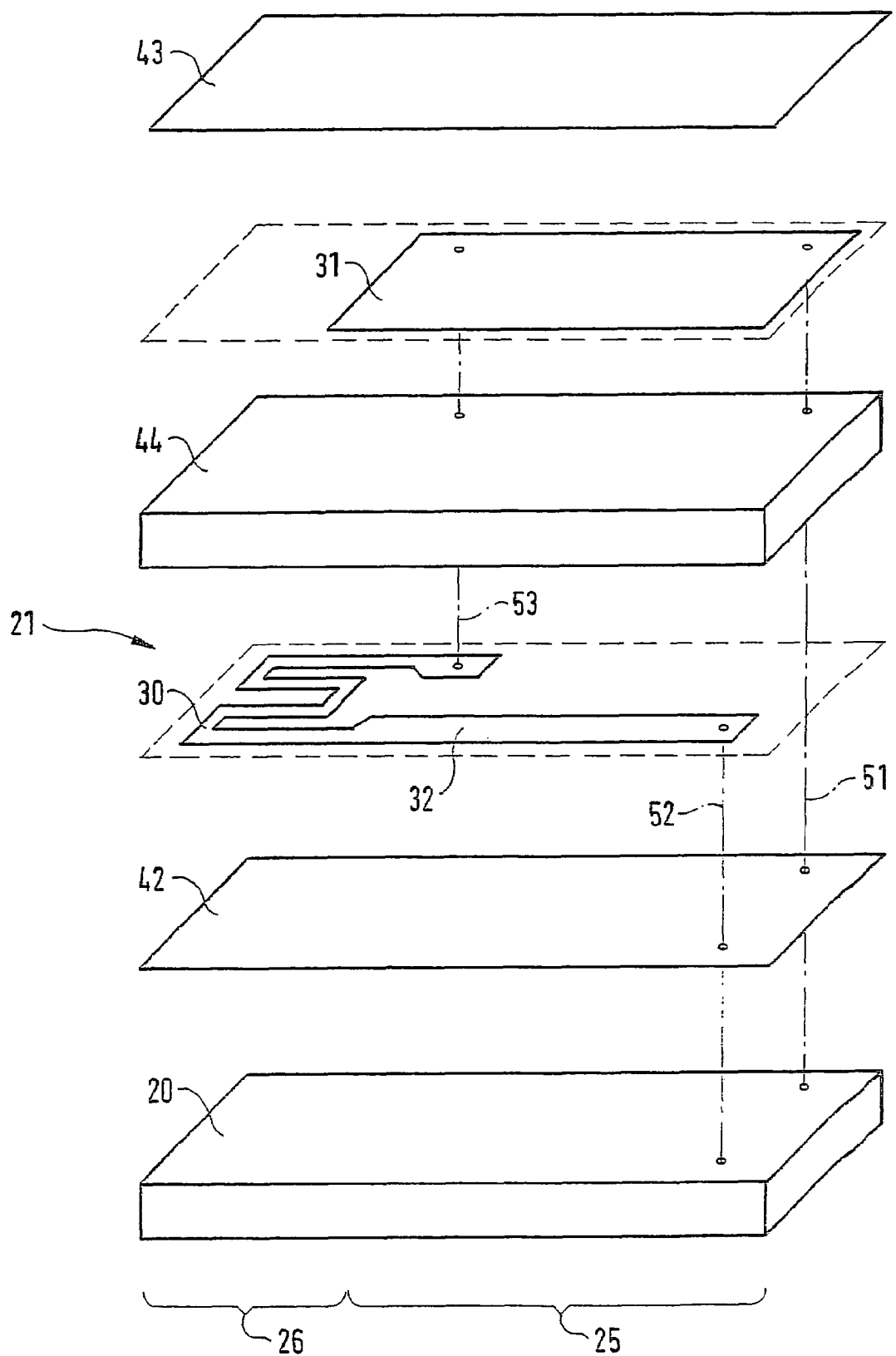
FIG. 3 shows an exploded view of a partial region of a second exemplary embodiment of a sensor element according to the present invention.

FIG. 3 shows a second exemplary embodiment of the sensor element according to the present invention in which mutually corresponding elements are identified by reference numerals matching those in FIG. 1. The second exemplary embodiment differs from the first exemplary embodiment shown in FIG. 1 in that, to insulate first from second heater supply lead 31, 32, no printed first insulation layer 41 is used, but an insulation foil 44 similar to carrier foil 20. In this way, insulation foil 44 separates first heater supply lead 31 from heater 30 and from second heater supply lead 32. Insulation foil 44 extends across the entire large surface of the sensor element. The contacting of heater 30 to first heater supply lead 31 is implemented via a third plated through-hole 53 introduced in insulation foil 44.

To produce the second exemplary embodiment of the sensor element, the following are printed (in this sequence and using screen-print technology) onto carrier foil 20: second insulation layer 42, heater 30 having second heater supply lead 32. First heater supply lead 31 and third insulation layer 43 are printed onto insulation foil 44. After printing, carrier foil 20 and insulation foil 44 are laminated together with solid-electrolyte foils 61, 62 of measuring device 22 and then sintered. First heater supply lead 31 may also extend into the region of heater 30 or across the entire large surface of sensor element 10.

In another embodiment of the present invention (not shown), the heater may be arranged in the same plane of stratification as the first heater supply lead, which is at a constant potential, and/or it may form a continuous circuit trace with the first heater supply lead, while the second heater supply lead is provided in a plane of stratification on the side of the first heater supply lead facing away from the measuring device. For the contacting of the second heater supply lead to the heater, a contact point or a plated through-hole is provided as it is in the specific developments shown in the figures.

Heater 30 and first and second heater supply leads 31, 32 have platinum with a ceramic portion, for instance. The main component of first, second and third insulation layer 41, 42, 43 is aluminum oxide, for example. First and second solid electrolyte foil 61, 62 are made mainly of yttrium-stabilized zirconium oxide. Carrier foil 20 and insulation foil 44 include, for instance, yttrium-stabilized zirconium oxide and/or aluminum oxide. If carrier foil 20 is made of aluminum oxide, second insulation layer 42 may be omitted.

In accordance with the present invention, first heater supply lead 31 is at a largely constant potential, such as ground potential. However, it lies in the discretion of one skilled in the art to connect first heater supply lead 31 to another largely constant potential, for instance if this is more advantageous for reasons of circuit engineering. A largely constant potential of first heater supply lead 31 within the meaning of the present invention is to be understood as a potential that, compared to the potential of second heater supply lead 32, is subject to only slow and/or slight changes and thus does not cause any, or only low, induced voltages into measuring device 22. That is to say, the induced voltage into measuring device 22 due to potential changes at first heater supply lead 31 is to be considerably lower than the induced voltage that would occur at second heater supply lead 32 due to the potential changes if it were not shielded by first heater supply lead 31, which is at an at least largely constant potential.

What is claimed is:

1. A sensor element, having a layer configuration, for detecting a concentration of a gas component in an exhaust gas of an internal combustion engine, comprising:
    a measuring device configured to detect a physical property of the gas; and
    a heating device including a heater, which is electrically connected to a first heater supply lead and a second heater supply lead;
    wherein the first heater supply lead at least largely covers a full surface of the sensor element in at least one of a supply region and a region of the heater, and is arranged in a plane of stratification between the second heater supply lead and the measuring device and the first heater supply lead is at an at least largely constant electrical potential.

2. The sensor element as recited in claim 1, further comprising:
    an insulation layer, the first heater supply lead being insulated from the second heater supply lead by the first insulation layer;
    wherein the heater has a contact point via which the heater is electrically connected to one of the first heater supply lead or the second heater supply lead, the first insulation layer having a recess in a region of the contact point.

3. The sensor element as recited in claim 1, further comprising:
    a carrier foil, at least one of the heater and the second heater supply lead being electrically insulated from the carrier foil by a second insulation layer;
    wherein at least one of the heater and the first heater supply lead is electrically insulated from the measuring device by a third insulation layer.

4. The sensor element as recited in claim 1, wherein the heater, the first heater supply lead, the second heater supply lead, and insulation layers are applied onto a carrier foil using screen printing.

5. The sensor element as recited in claim 1, further comprising:
    an insulation foil, the insulation foil being arranged between the first heater supply lead and the second heater supply lead, wherein the heater is electrically connected to at least one of the first heater supply lead and the second heater supply lead via a plated through-hole in the insulation foil.

6. The sensor element as recited in claim 1, wherein the first heater supply lead is at a constant potential, and, to heat the sensor element, a potential of the second heater supply lead is configured to be modified by electrical circuit elements arranged outside of the sensor element.

7. The sensor element as recited in claim 6, wherein the first heater supply lead is at a ground potential.

8. The sensor element as recited in claim 1, wherein the measuring device includes at least one electrochemical cell having a first electrode, a second electrode and a solid electrolyte, the solid electrolyte electrically connecting the first electrode and the second electrode.

9. The sensor element as recited in claim 1, wherein at least one of the first heater supply lead and the second heater supply lead has a lattice structure.

10. A sensor element, having a layer configuration, for detecting a concentration of a gas component in an exhaust gas of an internal combustion engine, comprising:
    a measuring device configured to detect a physical property of the gas; and
    a heating device including a heater, which is electrically connected to a first heater supply lead and a second heater supply lead;
    wherein the first heater supply lead is arranged in a plane of stratification between the second heater supply lead and the measuring device and the first heater supply lead is at an at least largely constant electrical potential; and
    wherein a perpendicular projection of the second heater supply lead onto the plane of stratification of the first heater supply lead lies at least regionally on the first heater supply lead.

* * * * *

UNITED STATES PATENT AND TRADEMARK OFFICE
CERTIFICATE OF CORRECTION

PATENT NO. : 7,628,900 B2  Page 1 of 1
APPLICATION NO. : 10/500661
DATED : December 8, 2009
INVENTOR(S) : Springhorn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1297 days.

Signed and Sealed this

Second Day of November, 2010

David J. Kappos
*Director of the United States Patent and Trademark Office*